United States Patent [19]
Bartos

[11] Patent Number: 5,846,548
[45] Date of Patent: Dec. 8, 1998

[54] COMBINED ADMINISTRATION OF MITOGENIC IMMUMO STIMULATOR AND A THYMOMIMETIC

[75] Inventor: Stefan Bartos, Soligen, Germany

[73] Assignee: Bartos Patent Development & Holding Company Ltd., Dublin, Ireland

[21] Appl. No.: 506,046

[22] Filed: Jul. 24, 1995

Related U.S. Application Data

[63] Continuation of Ser. No. 320,401, Oct. 3, 1994, abandoned, which is a continuation of Ser. No. 776,367, filed as PCT/EP90/00868, May 31, 1990, abandoned.

[30] Foreign Application Priority Data

Jun. 1, 1989 [DE] Germany ............................ 39 17 852.8

[51] Int. Cl.$^6$ .................. A61K 31/00; A61K 39/385; A61K 35/55; A01N 65/00
[52] U.S. Cl. ...................... 424/278.1; 424/195.1; 424/568; 514/1; 514/12; 514/13; 514/14; 514/15; 514/16; 514/17; 514/18; 514/21; 514/23; 514/24; 514/53; 514/54
[58] Field of Search ........................ 514/1, 12–18, 514/23, 21, 24, 54, 53; 424/195.1, 278.1, 568

[56] References Cited

U.S. PATENT DOCUMENTS

| | | |
|---|---|---|
| 3,267,090 | 8/1966 | Mueller . |
| 4,529,543 | 7/1985 | Renoux et al. .................. 260/112 |
| 4,548,813 | 10/1985 | Lawson . |

OTHER PUBLICATIONS

Cupissol et al, 1981, C.R. Seances Soc. Biol. Ses Fil. 175(2):235–41 Abstract only.
Ganguly et al, Chemotherapy, 1994, 40:272–278.
Hajito et al, 1989, Cancer Res. 49:4803–4808.
Serrou et al, 1979, NYAS, 95–100.
Hajto, 1986, Oncology, 43 (suppl 1):51–65.
Kuttan et al, 1992, Cancer Letters, 66:123–130.
Umiel et al, 1978, Cellular Immunol, 37:134–141.
Kuttan et al, 1992. J. Expt. Clin. Cancer Res. 11(1):7–12.
Walzel et al, 1990, Folia Biologica (Praha), 36:181–187.
Jonas et al, 1992. Acta histochimica, (Suppl.–Band XLI, S):73–79.
Kuttan et al, 1988, Cancer Letters, 41:307–14.
von Laue et al, 1988, Deuusche Zeit. fëur Onkelogie, 3:68–72.
Franz 1986, Onocology 43 (Suppl. 1):23–34.
Wannagat 1991 Reflections on Cancer Therapy. Mater. Med. Pol. 23(4):249–250.
Evett et al. 1986. Biological Properties of Pyrularia thionin . . . Toxicon 24(6):622–25.
Dillman et al. 1987. Phase II Trial of Thymosin Frachion 5 . . . J. Biol Resp. Modifiers. 6:263–267.
Irimajuiri et al. 1979 Effect of Ok 432 and Thymosin . . . Med. J. Kinki Univ. 4(2):191–199 Abstract only.
Hadden et al. 1989. Therapy of secondary T–cell immuno-deficiencies with . . . Med. Oncol. & Tumor Pharmacother. 6(1):11–17.
Nedwin et al. 1985. Effect of Interleukin 2, Interferon—8, and mitogens . . . J. Immunol. 135(4):2492–97..
Aymon. 1990. Mistletoe in advanced cancer. Cancer Journal. 3(3):123.
Umil et al (1978) Cell Immunol. 37(1):134–141, Abstract only.
Hauser (1989) Schweiz Rundsch Meu Prax 78(17): 498–506, Abstract only.
Kienle (1981) Z FA (Syottgart) 57(5):328–337, Abstract only.
Leroi (1979) Krebsgeschehen 11(5):145–146, Abstract only.
Franz (1985) Pharmazie (40,2 97–104), Abstract only.

*Primary Examiner*—N. M. Minnifield
*Attorney, Agent, or Firm*—Jacobson, Price, Holman & Stern, PLLC

[57] ABSTRACT

A method of tumor therapy involves controlling the immune system by co-administration of a mitogenic immuno-stimulating substance and a thymomimetic substance.

1 Claim, 7 Drawing Sheets

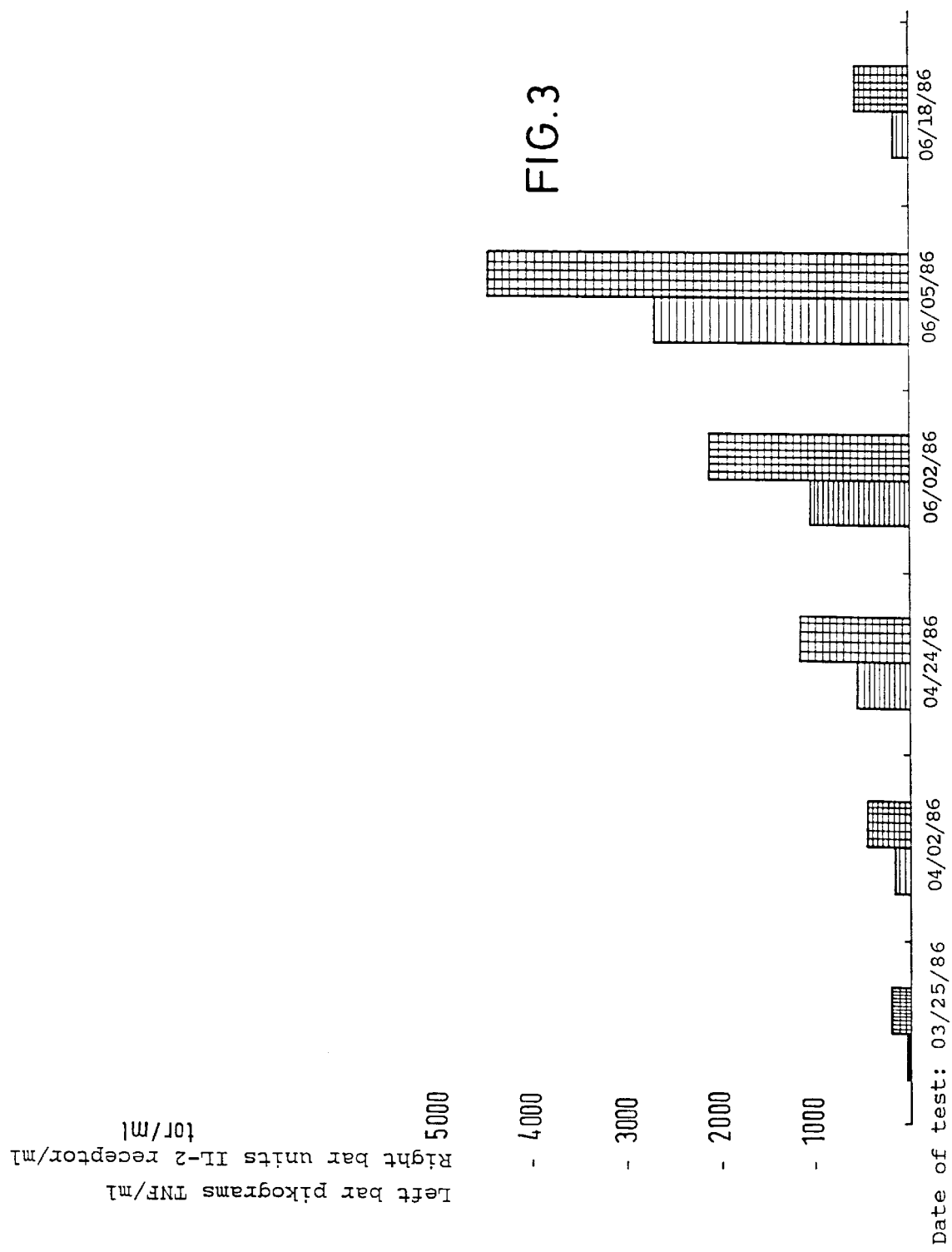

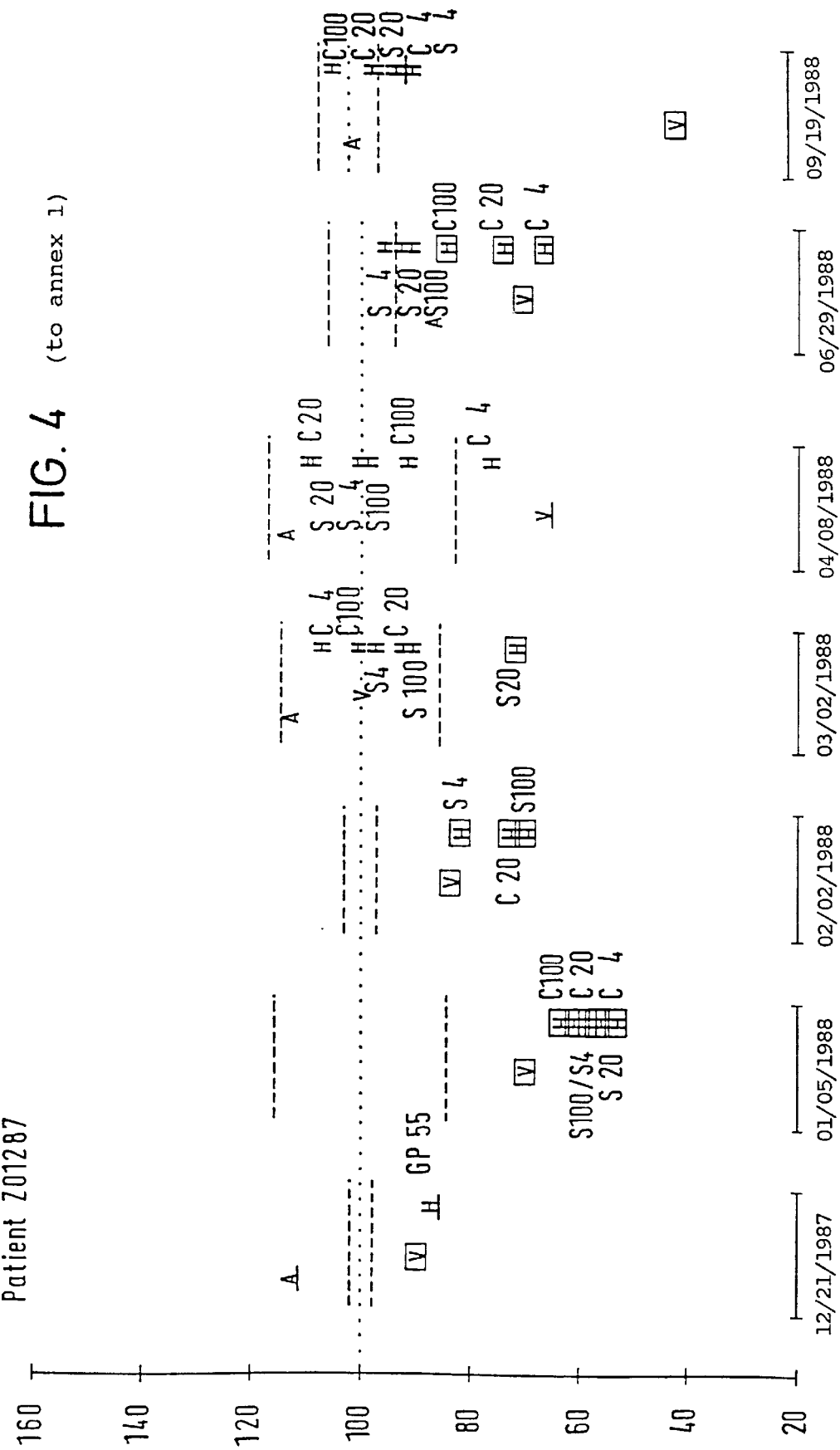
FIG. 4 (to annex 1)

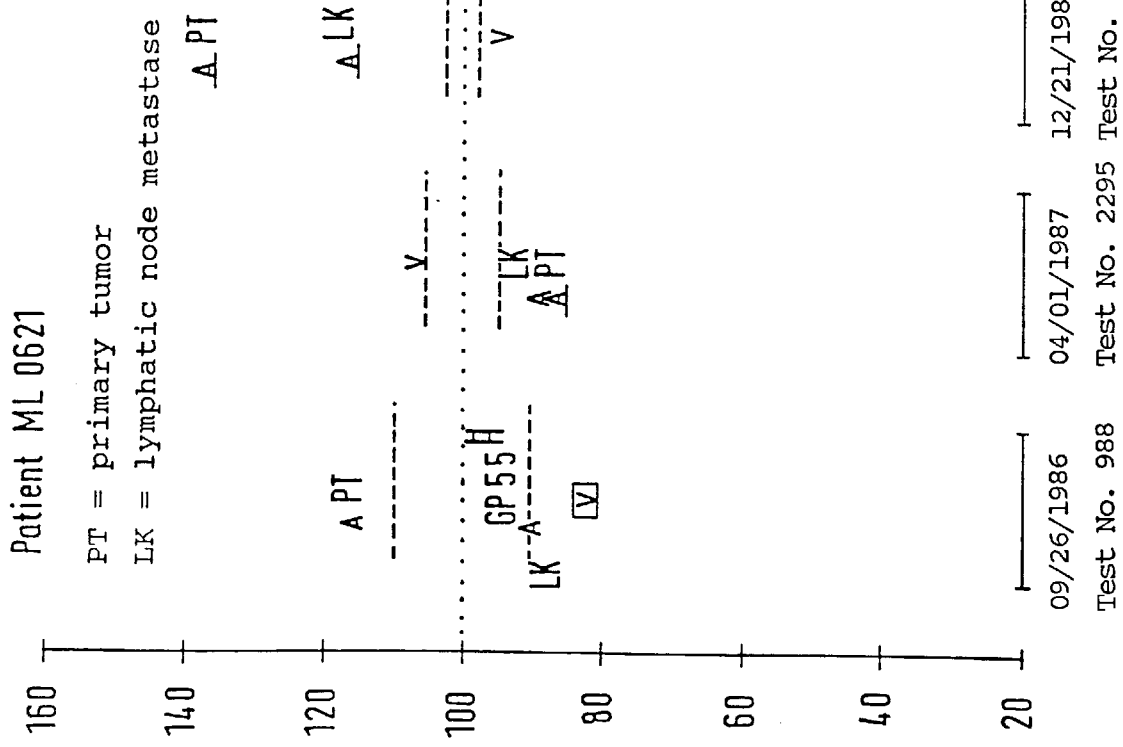

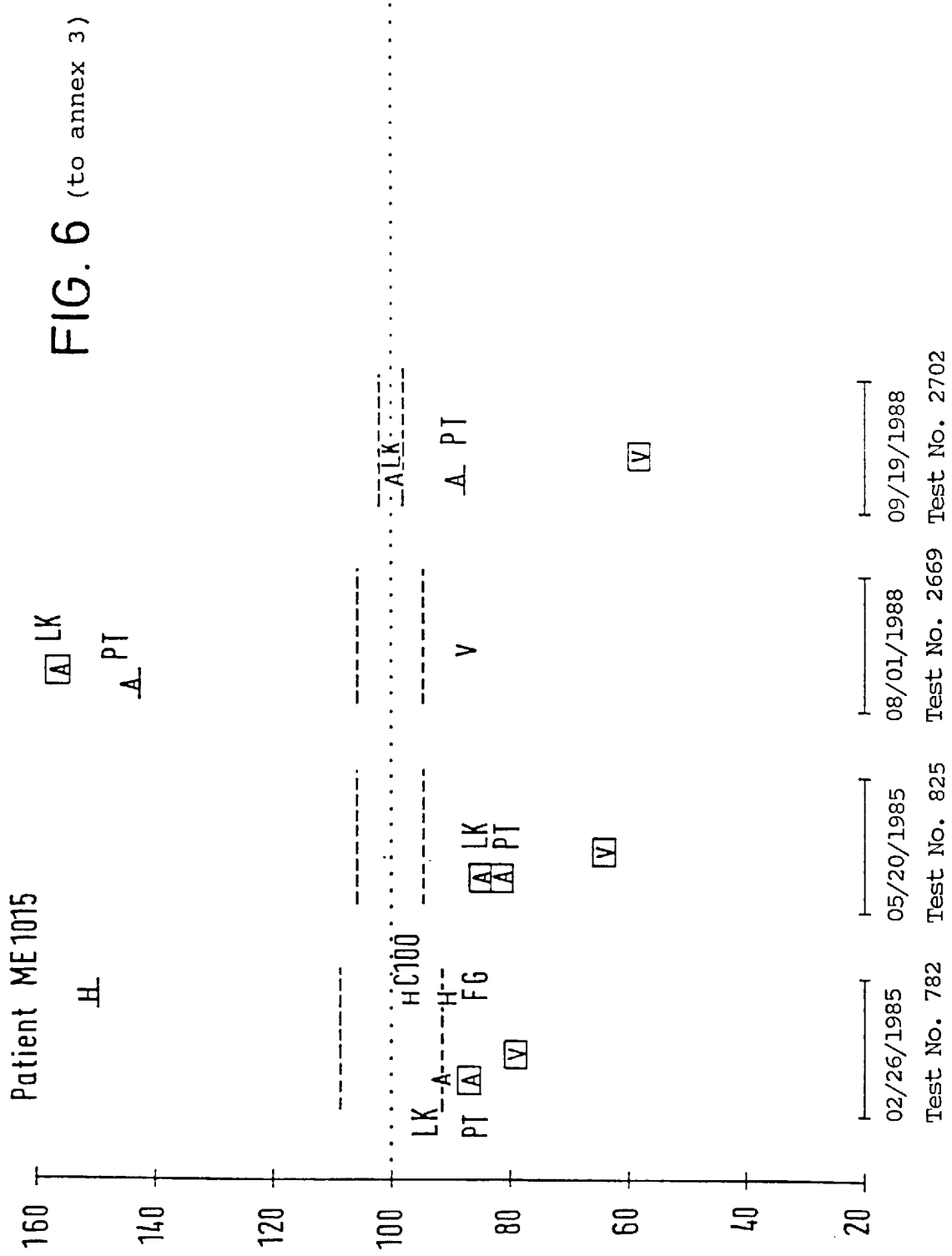
FIG. 6 (to annex 3)

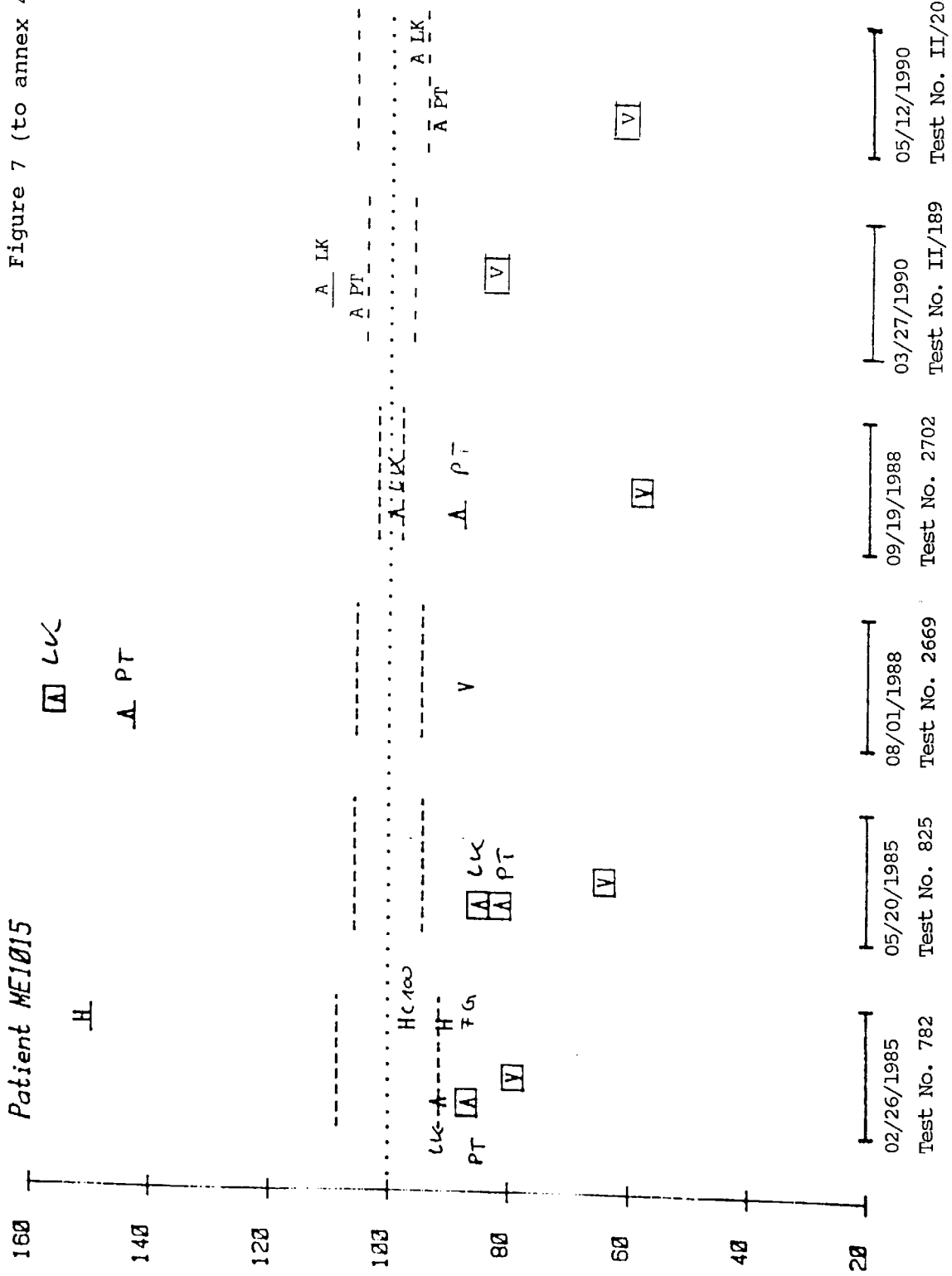
Figure 7 (to annex 4)

COMBINED ADMINISTRATION OF MITOGENIC IMMUMO STIMULATOR AND A THYMOMIMETIC

This application is a continuation of application Ser. No. 08/320,401, filed Oct. 3, 1994 now abandoned, which is a continuation of application Ser. No. 07/776,367, filed as PCT/EP90/00868, May 31, 1990, now abandoned.

Subject matter of the present invention are preparations of combinations of compounds for tumor therapy with controlled and regulated immune system and the use of corresponding individual substances for the preparation of drugs for combined application in tumor therapy with controlled and regulated immune system. Furthermore, this invention relates to the method of tumor therapy with controlled and regulated immune system by combined application of active substances, and a procedure for improving control of the immune system prior to and during tumor therapy, in particular with the aid of active substances used according to the invention.

In recent years, there has been steadily growing knowledge about the presence of the immune system and its mode of action. At the same time, the recognition gained acceptance that very many diseases have immunological causes, and that very many diseases can be analyzed and be therapeutically influenced favorably, or even be favorably affected therapeutically using immunological techniques.

Immunology is a relatively young science experiencing a very rapid development. A good survey regarding the present state of art in immunology is given in "Das Kurze Lehrbuch der Immunologie" by Ivan Roitt, Jonathan Brostoff, David K. Male, in the German translation by Ihor Harabacz, Georg Thieme Verlag, 1987, Stuttgart/New York, ISBN 3-13-702101-4.

Likewise, intense work has been done in the field of tumor immunology in recent years, therapeutic success, however, being small so far. Difficulty and complexity of the facts can, i.a., be seen from the book "Immunologie und Tumormarker beim Mammakarzinom", ed. U. D. Koenig, Ferdinand Enke Verlag, Stuttgart, 1933, ISBN 3-432-93471-8. Useful and simplified ways of a preparatory and concomitant immunological examination are found in the patent applications by the same applicant concerning "Verfahren zur integrierten onkologischen Eingangsuntersuchung und Krebstherapie", German laid-open patent application 3,719,698 and WO 88/09935 (PCT/EP88/00509).

Herein, it is stated, i.a., that the tumor-associated immune response is not privileged. Put in a simple way, it can be stated that the first step in the clash between tumor host and cancer cells likewise takes place on the level of macrophages and natural killer cells, and then in co-action with functionally different subpopulations of the T-cells. Not until then occurs a B-cell immune response, with appearance and detectability of tumor-associated antibodies, generally with the immunoglobulin types IgM, IgA, and IgG.

The tumor-associated antibody may in turn enhance cellular cytotoxicity against the tumor cells. It is known to all experts that maximum efficiency may be assigned to an antibody-controlled, complement-depending, cellular cytotoxicity, where antibodies of the type IgM and/or IgG are detectable.

Only the clarification of quality and extent of a tumor-associated cellular and humoral immunity eventually provides information about which additional prognostic criterion is represented by the tumor-associated immune reaction, and which additional therapeutic potential it comprises.

In cancer therapy, there are inevitably demanded immuno-biological initial and control examinations to be conducted as a routine. Blind, uncontrolled specific immunotherapy or simple nonspecific stimulation therapy using immune modifying substances must be strictly rejected, and for several reasons is designated as being dangerous. Any biological therapy is a double-edged weapon which may cause both desired and undesired effects with the same patient.

Thus, using different examination techniques, both a solely cellular and a solely humoral immune response, or an antibody-controlled cellular cytotoxicity can be measured nowadays, actually as such, as well as a tumor-associated immune reaction directed against cancer cells, using, for example, the above-mentioned method WO 88/09935 ex vivo/in vitro. Even today, highly significant prognostic statements can be assigned to such examination results; cf., U. D. Koenig, in Vol. 12 of "Klinik der Frauenheilkunde, Spezielle Onkologie III", pp. 281–326, ISBN 3-541-1520-X.

Credit is due to U. D. Koenig and his group for having realized that the leukocyte migration inhibition assay (LMI) not only is an examination procedure for detecting T-cell-dependent, adoptive, cellular immunity which is established in text books, but that both forms of reaction in the LMI assay, namely a significant migration inhibition and a significant migration enhancement as positive forms of reaction—beside negative reaction—must be considered, and that these, in the same patient, depending on disease status, general immune resistance, and therapeutic measures such as chemotherapy and/or irradiation, may merge into one another.

Migration enhancement is to be treated as equivalent to immune tolerance, and it means that immune defense has lost control over cancer growth. This condition is associated with a very poor prognosis, and with mammary carcinoma is de facto a death sentence for the patient. Anglo-Saxon authors such as Zachrau et al., hitherto have failed to notice this fact by not having recognized the LMI enhancement reaction form as being a positive reaction, but started out from the assumption that with metastasizing cancer, the tumor cells had lost their antigenicity, and for that reason, metastases could form, since the positive reaction (inhibition) can no longer be determined in the LMI assay. On the contrary, it is noted that with metastasizing cancer, and likewise with carcinoma of the breast, there is exclusively found the enhancement result picture in the LMI assay. Just how important this recognition is for the assessment of inhibition and enhancement as positive forms of reaction in the LMI assay with differing prognostic, immunological expression can be documented on the basis of a recent scientific publication: D. Jenkins, H. O. Douglass, Jr., M. H. Goldrosen: "Role of T-Cells in the Human Leukocyte Adherence Inhibition Assay", Tumor Diagnostik & Therapie 8 (1987), pp. 204–209.

The leukocyte adherence inhibition assay (LAI) likewise represents an established method for detecting immune response. While the authors describe a complicated in vitro experimental procedure revealing what kind of role the suppressor T-cells play in the reaction failure in the LAI assay, and even show inhibited and enhanced adherence of leukocytes in table form, they do not recognize that also increased adherence such as the enhanced reaction in the LMI assay is to be taken as a positive reaction. As soon as the authors lysed away the suppressor T-cells from the population of the isolated defense cells, inhibition of adherence also occurred with negative (enhancement) samples, and thus, positive LIA reaction.

This should be taken to indicate that both positive forms of reaction in the LMI assay are not representing a privilege of the leukocyte migration inhibition assay in the meaning of inhibition and enhancement, but that here a generally valid finding is encountered. Thus, not only the LMI assay but also the LAI assay could be used for monitoring the tumor-associated immunological reaction in the cancer disease as a qualitative and quantitative ex vivo/in vitro assay. For practical pragmatic reasons, however, the LMI assay is applied, since several groups using this assay system over a period of 20 years have obtained the same results which therefore are deemed as being scientifically and basically-medicinally reliable on an international level.

From the above-mentioned WO 88/09935, it can be seen what significance to tumor immunology lies in establishing an autologous control and assay system. At the same time, it is demonstrated how to efficiently obtain autologous antigen/vaccine from patient tumor tissue/material in biologically native form for tumor-immuno-biological ex vivo/in vitro beginning and control examinations, even prepared in skin assay and vaccine quality.

Here, it is essential that by simultaneous use of dissolvable antigen fraction (cytosol) and non-dissolvable antigen fraction (tumor sediment/cell membrane), the full antigen spectrum of a tumor cell is included and covered, in a way that even depending on reaction failures it can be differentiated where the major amount of antigenicity is located, namely within the cell interior or within the cell membrane. These statements are confirmed by first results using the example of breast and ovary carcinomas [Stefan Janke and coworkers: lecture in the 6th Hearing on Tumor Immunology at the Institute of Gynaecological Oncology, held on Jun. 12, 1988, at Homburg an der Saar, and J. Reinsberg and coworkers: "Carinoembrionic Antigen (CEA), CA-15-3 and TPA in the Cytosol of Breast Cancer Patients", lecture in the 7th Hearing on Tumor Immunology at the Institute of Gynaecological Oncology, held on Dec. 9 and 10, 1988, at Heidelberg, publications in preparation or being printed).

By cytosol/CEA determination, three basic types of mammary carcinoma may be discerned: group 1 (type O), group 2 (type A), and group 3 (type B). The cytosol CEA concentration per mg corrected tumor protein between from 0.0 to 0.25, between from 0.25 to 4.0, and above 4.0 ng CEA/mg corrected tumor protein represents three distribution curves each representing one biotype of mammary carcinoma. Group 2 (biotype A) breast carcinoma patients show, in very significantly increasing numbers of up to 49%, an immunological cross-reaction in the LMI assay versus coat protein gp 55 from mouse mamma carcinoma virus (MMTV) type Paris III. In contrast thereto, with mammary cancer patients from group 1 and 3, only up to 11% and up to 19%, respectively, show reaction versus gp 55. For this reason, and due to other immunological/virological data, mammary carcinoma biotype A is also referred to as retrovirus-associated mammary carcinoma.

It is an interesting discovery that with mammary carcinoma biotype A, the major amount of antigenicity comes from the interior of the cell, i.e., from the dissolvable cytosol portion, and it frequently occurs that with this biotype, antigenicity against the cell membrane fraction has already been lost and is no longer detectable in the LMI assay, although strong reaction against the cytosol antigen fraction still can be noted. This phenomenon is very important, since defense cells are capable of recognizing vital tumor cells as being foreign and can attack them only when antigenicity is located within the cell membrane. In contrast, with mammary carcinoma biotype B and with ovarian carcinoma, there is always found antigenicity both within the cell membrane and in the cytosol fraction. An explanation for this different reaction is that with retrovirus-associated mammary carcinoma, tumor antigenicity and tumor antigens most probably are gene products of one virus genome or are caused by same. In contrast, with ovarian carcinoma and mammary carcinoma biotype B, undifferentiation antigens in the cell membrane are predominantly found.

Using the antigen preparation according to WO 88/09935 in the example of mammary carcinoma for the LMI assay, it was determined that it is strongly to be recommended to test using several different antigen doses for measuring the T cell-dependent, adoptive, tumor-associated immunity ex vivo/in vitro. For this purpose, three antigen doses each were used, preferably having 100, 20, and 4 $\mu$g of corrected cytosol protein per ml medium, and 100, 20, and 4 $\mu$l of standard tumor sediment $0.2\mu$ filtrate preparation per ml LMI medium. Here, increased positivity rate in the LMI assay regarding inhibition and enhancement was found, namely from 39.6% (21/53) in single testing to 77.3% (34/44) if at least two cytosol antigen doses and three tumor sediment antigen doses were used. 78.3 (18/23) was found where the assay could be run completely using each time three cytosol antigen and three tumor sediment antigen doses. The difference in positivity rate is highly significant (p lower than 0.001).

This improvement in sensitivity in the LMI assay by using several, preferably three suitable antigen doses is very important with the mammary carcinoma, since in this way, by using a single test procedure, virtually all of the immunologically active mammary carcinomas can be recognized already at the time of primary therapy. With clinically manifest metastasized mammary carcinoma using combinations of different immunological procedures, circulating immune complexes can be detected in a maximum of 75.3% of the cases, i.e., an immunological conflict of body and cancer disease (Krapf, F. D. and coworkers: "Nach-weis von zirkulierenden Immunkomplexen bei Mammakarzinom und malignem Melanom mit drei verschiedenen Methoden", Tumor-diagnostik & Therapie 3 (1982), p. 219.

In an earlier work, the inventor was able to show that by using indirect immunofluorescence, free, tumor-associated antibodies to the types IgG, IgM, and IgA can be detected on mammary carcinoma cells in 75% (21/28) of the cases already at the time of primary therapy; cf., D. S. Bartos: "Tumorassoziierte IgG-, IgM- und IgA-Antikörper an Mammakarzinomzellen und ihre mög-liche prognostische Bedeutung", Immunologie und Tumormarker beim Mammakarzinom, edt. by U. D. Koenig, Ferdinand-Elke-Ver-lag, 1983, Stuttgart, ISBN 4-432-93471-8, pp. 37–43. In accordance, IgA antibodies are found in 61% (17/28), IgM antibodies in 35% (7/20), and IgG antibodies in 22% (4/18) of all cases. Accordingly, it is definitely established, for instance, that in a great majority of the breast cancer cases, an antibody-controlled cellular immune response/cytotoxicity is already present at the time of diagnosis and primary therapy, and not only a solely cellular, tumor-associated reaction. Furthermore, it follows that both a cellular T cell-dependent immune reaction and an antibody-controlled cellular immune response are detected in the LMI assay.

It is technically very difficult and costly to isolate living tumor cells, particularly with mammary carcinoma, at a routine level, and to conduct further investigations with them. On the other hand, it is of immense prognostic and therapeutic importance to know at least qualitatively which type and intensity of a tumor-associated immune reaction is present. For this reason, using the example of mammary carcinoma, it was tried to detect the tumor-associated antibodies on mammary carcinoma cells simply by immunohistochemistry in paraffin sections, as these are prepared in histopathological diagnostics on a routine basis. These results were likewise reported at the 7th Arbeitsgespraech on Tumor Immunology at the Institute of Gynaecological Oncology, held on Dec. 9 and 10, 1988, at Heidelberg (S. Janke and coworkers: "Immunohisto-chemical Detection of Immunoglobulin Classes IgG, IgM, IgA and T-Cell-Dependent Tumor-Associated Immunoreaction in Breast Cancer Patients"). Results using this technique were widely identical: in 68.4% of the cases (13/19), there were found mammary carcinoma cells tumor-associated antibodies, in 57.8% of the cases (11/19) IgA, in 42.1% of the cases (8/19) IgM, and in 31.6% of the cases (6/19) IgG.

It is part of the propaedeutics in immunology that IgA antibodies are not as active and effective immunobiologically as are IgM and/or IgG antibodies. Thus, the most effective antibody-controlled cellular cytotoxicity must in general and tumor-associative be assigned to an immune reaction caused and controlled by complement-dependent IgG antibodies.

Tumor-associated immune defense may be influenced and enhanced by drugs for therapeutic purpose in various ways. Satisfactory therapeutic success, however, will be achieved only in cases where the above-mentioned implementations and criterions are considered as well.

In the case of an antibody-controlled cellular cytotoxicity which is even caused by complement-dependent, tumor-associated antibodies of the IgG type, being one of the most effective immune defense reactions, an immunostimulating substance or substance combination such as xyloglucan and arabinogalactan which are isolated from the aboveground parts of the medicinal plant Echinacea, will not be used for therapy and enhancement of the tumor-associated immune reaction and for breaking immune tolerance in case of tumor progression/relapse. Instead, an immunotherapeutic measure is used which enhances the antibody-controlled cellular cytotoxicity in such way that, if possible, even immune tolerance is overcome, and migration inhibition instead of enhancement will be detectable in the LMI/LAI assay again. Only in this case, a therapeutic effect may be expected clinically. The active substances from the Echinacea plant cannot meet this purpose, as could be established clinically, since both polysaccharides xyloglucan and arabinogalactan are stimulating an immune response by the defense cells exclusively at the lowest level: macrophages and granulocytes. Xyloglucan specifically stimulates the white blood cells (granulocytes) and the macrophages (large phagocytes). The same effect is exhibited by arabinogalactan, though to a substantially lesser extent. This active substance, however, additionally stimulates the macrophages to release tumor necrosis factor (TNF). Currently, great efforts are being made by the pharmaceutical industry to use genetically engineered natural lymphokines, products of cells of the natural immune defense, likewise TNF, as well as interferons, interleukin 2, etc. in the clinic or in cancer therapy, and to work out indications for these novel individual products. So far, there has been a great disappointment. Recently, results of a study on TNF were published. Applying TNF in 400 cancer patients, a slight effect could be determined in only 5 to 10% of the cases, with severe side effects.

Considering the above explanations, it becomes clear why these efforts are condemned to failure from the very start. Most of the lymphokines preparable by genetic engineering such as TNF, interleukin 2, interferon, are nothing but messenger and enhancer substances of natural immune defense. Thus, it is obvious that first of all, using autologous assay systems, it should be determined for any single cancer patient if a defense reaction, namely a tumor-associated immune reaction is present at all. If present, then it must be determined in which quality and intensity, and on which level of the cascade of the complicated immune defense system there is something present. Only subsequent to determination and availability of these data, a suitable stimulating substance or combination of substances should be chosen and applied for purposeful therapy. Required technique and knowledge are now available. Thus, it is merely a question of resources and intention, to proceed purposefully and successfully in this area of cancer immunotherapy.

This is explained once more using the above-mentioned example arabinogalactan/TNF:

Here, two therapeutic principles will compete, namely substitution therapy and induction therapy. The price for Echinacea extract is substantially lower than for biotechnologically prepared TNF. Nevertheless, in many cases, Echinacea will release more TNF within the body of the patient than is economically possible in TNF substitution therapy. Good clinical long-term results were obtained worldwide in several groups with colorectal carcinoma and mammary carcinoma by inoculating/vaccinating tumor patients using autologous tumor cells/tumor material. Here, too, even better results may be achieved when the above-mentioned explanations are considered and only such patients are vaccinated who exhibit measurable tumor-associated immune reaction at all. Furthermore, vaccination will be conducted in a controlled manner, with the purpose to induce and maintain an effective defense reaction against the cancer cells. Thus, if possible, an antibody-controlled cellular immune reaction with complement-dependent tumor-associated IgG antibodies is aimed for.

A typical example for the developed principle of combined cancer therapy according to the invention with controlled and regulated immune system follows from the case of a patient suffering from incurable cancer outlined below, where tradition-medicinal standard therapy had been failing so far or had become ineffective. It is the case of a 58-year-old female breast cancer patient in winter 1985/1986:

On Oct. 17, 1985, the patient visited the medical director of the SEROBAC, Institute, the inventor, because in spite of treatment conducted by a senior physician in another hospital, cancer disease was proceeding. Primary therapy in 1979 was pT2a, primary tumor diameter 2.8 cm, 5 affected lymphatic nodes biotype B (CEA positive). At that time, on the basis of perioperative alpha 2 serum level analysis, assumption of immunological activity of tumor action. Ablatio mammae. 6 cycles of leukeran-methotrexate-5-fluorouracil according to record of the Düsseldorf mammary carcinoma study. 9 months after primary therapy, orbita metastasis left side betatron irradiation. 15 months after primary therapy formation of lung metastases with dyspnoea. Begin of a combined tamoxifen-clinovir therapy (3×10 mg tamoxifen plus 3×100 mg clinovir per os). Originally, a receptor-positive breast carcinoma was present: estrogen and progesterone receptors moderately positive. Full remission upon hormone therapy. After three years, since clinically radiologically NAD (CT thorax, head, abdomen and bone scintigram), hormone therapy was ended by other physicians. After further 1¼ years, in autumn 1984, skin nodules/skin metastases appeared. Positive bone scintigram in February 1985. Tamoxifen prescribed again. Until October 1985, skin metastases grew further (about 20 to 25), largest at head, left neck area, up to chestnut size. High dose MPA therapy trial. Temporary drop of CEA serum level increase. On Oct. 15, 1985, removal of two skin metastases of cherry size from the dorsum, prevertebral. Hormone receptor status positive for estrogen and progesterone receptors. Tumor cytosol and tumor sediment residues were processed to antigen. On Oct. 17, 1985, LMI assay: positive tumor-associated immune reaction with migration enhancement, as is usual with clinically manifest metastasized mammary carcinoma. Good general immune reaction to recall antigen streptokinase/streptodornase (V sign in FIG. 2). From Dec. 31, 1985 on, begin of systematic intravenous application of mistletoe total extract (Visci albi herba) following express request of patient, after all tradition-medicinal therapeutic possibilities were exhausted and had become ineffective. The commercial preparation Plenosol®, of the company Dr. Madaus & Co., Cologne, was applied. Plenosol®, is a mistletoe total extract. Adjustment of preparation intensity is done over decades via the so-called necrosis units. The preparation or plant extract is injected into the skin of rabbits, and here, at this spot, a reddening forms, the diameter of which may be determined by measurement. Thus, it is not so much a matter of skin necrosis units but of quantifying a local, sterile inflammation reaction including skin reddening and skin induration, since skin necrosis only forms with highest concentration.

The authors Dinkelaker and Kass in their book "Die Mistel in der Therapie" (Haug-Verlag 1982, ISBN 3-7760-0655-2) recommend, among other, intravenous therapy in cancer patients as a nonspecific irritation therapy in the sense of an anthroposophic approach using increasing doses up to 3 months, and then the highest dosage of 700 NE (necrosis units), i.e., 0.7 ml of ampoule intensity I having 1000 NE/ml. With lung and bronchial carcinoma, the authors on page 55 indicate an ultimate dose of from 0.3–0.5 up to 1.0 ml PLENOSOL, intensity II to be reached. Traditional physicians reject the use of mistletoe extracts as drugs in cancer therapy. This also has been verified in court disputes where the point was treatment costs of mistletoe therapy.

From Dec. 31, 1985 on, the above patient was subjected to application of the mistletoe preparation Plenosol®, intensity II per ampoule per week, i.e., 20,000 NE per week, intravenous. At the same time, the tumor-associated immune reaction in the LMI assay and the total lymphocyte number were determined. Total T cell number and functional subgroups of lymphocytes, helper cells, suppressor cells, and natural killer cells (NK cells) were determined continuously. Effect on tumor activity was documented via serum CEA tumor marker level, and could be observed in skin metastase behavior (cf., FIGS. 1 and 2).

On Feb. 20, 1986, the tumor-associated immune reaction was controlled, after the patient subjectively felt somewhat better. Nevertheless, there was a continuous increase in serum CEA level. An amazing effect of mistletoe therapy occurred in the LMI assay. On Feb. 20, 1986, the mistletoe preparation was dosed higher in order to reach the limits of the therapeutic effect. One ampoule PLENOSOL, intensity II was applied daily, intravenous. LMI assay control showed increase of migration inhibition, i.e., breaking of immune tolerance and suppressor activities. Slight reddening about the skin metastases appeared. Computer sign A=reaction versus 20µ frozen tumor tissue section as the antigen source. Point lines H=various antigen doses from prepared tumor cytosol antigen and tumor sediment antigen. Single underline=single significant reaction versus control batch, each prepared three times. Squares=double significant reactions. From Feb. 25, 1986 to Mar. 11, 1986, application of 3×1 ampoules PLENOSOL, intensity II intravenous per week, and then, from Mar. 11, 1986 on, just 1×1 ampoule PLENOSOL, intensity II intravenous per week. LMI test batch versus varidase (=streptokinase and streptodornase) as recall antigens for measuring general immunity and for system control. Enhanced mistletoe therapy resulted in reddening about the skin metastases which intensified, while serum CEA and serum CA-15-3 increase dropped and became stationary. From Mar. 11, 1986 on, reset to dosage of Dec. 31, 1985, after a negative effect became visible, namely in the LMI assay and in damage to be seen in the total number of T cells, number of helper cells, and in part also the number of suppressor cells (cf. table 1). On Mar. 25, 1986, enduring and increasing negative-toxic effects with breakdown of general immunity (V sign), skin test Multitest®, Institute Merieux using pathological score (seven different bacterial and fungal antigens), in the LMI assay again migration enhancement/immune tolerance with disappearing skin reddening about the skin metastases, tumor marker serum level (CEA+CA-15-3) again increasing. Now, it was tried to combine the mistletoe preparation with a thymus preparation. This resulted in optimum mitogenic immunostimulation. Strong tumor-associated immune reaction was built up in the LMI assay with migration inhibition versus all tumor antigen doses and also traditionally, using tumor tissue section as the antigen source. Intense reddening about the skin metastases, disappearing of lentil-sized skin metastases and in part also larger tumor nodes up to bean size. Nodes of chestnut size grew significantly smaller. Drop of tumor marker serum level 5 to 7% per week. Partial remission in the bone scintigram. Patient subjectively did well now. She took up work again as an independent stationery dealer, although there were 150 to 250 g of tumor tissue present in her body at that time. No significant side effects in overall therapy up to now. There were applied 1 ampoule of Plenosol®, intensity II per week (20,000 NE) intravenous and 3×2 ampoules of THYM-UVOCAL, intramuscular. It was a thymus total extract of the company Dr. Mulli Nachfolger GmbH & Co. KG, Neuenburg (about 22 mg peptide mixture). Jun. 2 till Jun. 5, 1986: increase of drug dosage to 1×1 ampoule of Plenosol®, intensity II daily, keeping the dosage of THYM-UVOCAL, constant. Subsequently, additional increase of tumor-associated immune reactions clinically as well as ex vivo/in vitro. Jun. 5 till Jun. 18, 1986: the mistletoe preparation is taken out of the drug combination while at the same time, application of the thymus preparation THYM-UVOCAL, 3×2 ampoules per week, intramuscular, is continued. Immediate drop in tumor-associated immune reactions, clinically and ex vivo/in vitro, measurable in the LMI assay and detectable. Clinically, decrease and disappearance of the reddening about the skin metastases. Again, increasing tumor marker serum level and reappearance of formerly disappeared lentil-sized skin metastase nodules, size increase of larger tumor nodes.

From this case, as well as from a number of other meanwhile investigated cases, the inventor is gaining the following new conclusions: in plant extracts, but also in some animal extracts such as snake toxins, there must be present immunopharmacologically highly active substances increasing tumor-associated immune reaction in such a way that the corresponding functional subgroups of the lymphocytes are activated, and predominantly, the cytotoxically active lymphocyte subpopulations. Also, this activation process is capable of overcoming immune tolerance effected by suppressor substances and suppressor cells (as detectable in the LMI assay or in the LAI assay ex vivo/in vitro), and capable of re-establishing cell-mediated and antibody-dependent cell-mediated cytotoxicity, in spite of antigen persistence, and, in addition, capable of increasing the defense reaction to a considerable extent. Hitherto investigated immunopharmacologically active substances almost exclusively belong to the group of polysaccharides and lectins. Lectins are glycoproteins of plant or animal origin having sugar specificities. Being larger molecules, they have the functional property, similar to antibodies, to recognize their receptors or ligands according to the keyhole/key principle, like antibodies the corresponding antigens. Accordingly, these lectins appear to carry an important biological signal transmitting function. Substances being capable in vitro to trigger DNA novel synthesis, and hence, H3 thymidine incorporation (or possibly, trigger cell division) on suitable target cells such as human lymphocytes, are referred to as mitogenic substances. Classical representatives of these substances are the so-called mito-genic lectins such as concanavalin A (Con A) and phytohemagglutinin (PHA). Hitherto, these substances are utilized in in vitro immunological investigations to test capacity to be stimulated of defense cells of patients in various disease conditions, or that of test animals. In addition, mitogenic lectins were used in buffy-coat of blood donors (total isolated defense cells, including leukocytes), or in cultures of lymphatic continuous cell lines to be able to induce and biotechnologically prepare lymphokines such as interferon and interleukin 2. Such mitogenic lectins, however, have not been applied therapeutically in patients due to extremely high toxicity. The inventor, on the other hand, found that by removing the mistletoe lectins (mistletoe lectin I+II+III) from the mistletoe total extract, the immunopharmacological activity of the preparation Plenosol®, (mistletoe total extract) is lost almost completely.

If, in contrast, the mistletoe total extract is combined with thymomimetic substances, then it is possible to overcome immune tolerance, and to transform migration enhancement to migration inhibition in the LMI assay. Successfully tested as thymomimetic substances were the following: THYM-UVOCAL, intramuscular 3×2 ampoules per week, or, even more effective, 2–3×1 ampoule of TIMUNOX 100 subcutaneous with each 50 mg TP5. In 9 cases of breast cancer patients and 3 ovary cancer patients, this therapy has been successful, i.e., in 12 out of 12 cases. In each of these cases, the immunobiological ex vivo/in vitro initial and control examination were conducted using autologous tumor material as the antigen source (cf., WO 88/09935). Clinically, in all of the 12 cases, positive therapeutic activity could also be observed using the tumor symptoms. In contrast, in 4 out of 4 other cases, no significant activity was observed in the LMI assay with lectin-free mistletoe extract. Clinically, there was no improvement observed either. Thus, therapeutic activity lies in the above-described combination of immunopharmacological activity and effectiveness of the mistletoe lectins, as well as in the additional application of thymomimetic substances. This was confirmed by in vitro experiments, where both mistletoe total extract and isolated mistletoe lectin mixtures trigger mitogenic activity depending on dosis; they stimulate incorporation of H3 thymidine into normal or stimulated lymphocytes as well, and frequently even effect lymphokine production. This can be determined and verified in vitro by total lymphokine response and by influence on migration of isolated leukocytes.

The mistletoe lectins I, II, and III have the specifications galactose, galactoside, lactose, and melibiose. This may be determined by simple adsorption chromatography, for example, by the well-known coupling of these sugars to suitable sepharose preparations which remove corresponding lectins from the mistletoe total extract. Thus, therapy using mistletoe total extract is to be regarded as mitogenic immunostimulation which is therapeutically active in vivo as well. Here, it must be noted, however, that these active substances are lymphocyte-consuming. According to the invention, this is compensated by additional application of thymomimetic substances.

The familiar and recommended intravenous Plenosol®, monotherapy has a maximum dosage of 700 necrosis units per application. If mistletoe total extract is utilized in said dosage in clinical therapy, the cellular antibody-controlled immune reaction, however, can be increased only slightly. Likewise, using such dosage, it is not possible to convert immune tolerance/enhancement to inhibition, and to achieve a clinically measurable therapeutic effect in this way.

If, in contrast, therapy using mistletoe total extract exceeds the recommended amounts, stronger immunopharmacological effects are in fact obtained, but these are markedly lymphocyte-consuming. It is not sufficient in this case to apply an only weakly active thymus preparation in the recommended amount. Rather, it is necessary either to dose higher or to employ a more active thymomimetic drug. Thus, besides the total thymus preparation THYM-UVOCAL, already mentioned, use of a totally synthetic thymus peptide such as the preparation TIMUNOX 100 of the company CILAG containing 50 mg of the active substance TP5 is also possible.

Other suitable thymomimetic substances are the tetra- and tripeptides TP4 and TP3 of the company Richter Gedeon, Budapest. These are even shorter peptide fragments of the thymus hormone consisting of 38 amino acids from which TP5 has been derived. The combination of 66.7 mg of TP4 and 33.3 mg of TP3 per ampoule per application, subcutaneous twice to three times a week has proven particularly effective, namely in combination with the mistletoe total extract (PLENOSOL,). Moreover, the mistletoe total extract is dosed higher than recommended by the manufacturer. Here, the above-described immune system controls are always to be conducted.

The substance thymosin-α-1 of the company Hoffman LaRoche, Basel, a fully synthetic thymus hormone consisting of the total chain of 28 amino acids and being tested so far, might turn out to be another thymomimetic substance.

In the course of the above investigations another interesting observation was made: during mitogenic immunostimulation of cancer patients (effected by the mistletoe total extract PLENOSOL, and thymomimetic substances such as THYM-UVOCAL, and TIMUNOX 100), a moderate but highly significant (p smaller than 0.001) increase of eosinophilic granulocytes in the peripheral blood smear was regularly and reproducibly observed. Prior to therapy, the percentage of eosinophils is 1.7% (N=23 patients), and in the 6th week of immunotherapy 5.9% on the average. It is known that in clinical application of interleukin 2 prepared by genetic engineering, dosed highly, in application of a key lymphokine of T cells in the course of clonal expansion and the activation, there is likewise observed an increase of eosinophilic granulocytes in the peripheral blood smear regularly and very significantly, namely from 10 to 18%. Thus, it could be supposed that in the course of mitogenic immunostimulation, release and increased production of interleukin 2 likewise occurs, namely as an autocrine process or at least as an increase of interleukin 2 receptor density at the activated lymphocytes. Consequently, serum samples from the above-described patient which had been stored at −70° C. were examined for tumor necrosis factor and interleukin 2 receptor serum level concentration. Indeed, interleukin 2 receptor serum level concentration paralleled the clinical findings and the ex vivo/in vitro measurable reactions in the LMI assay. This indicates that by clinical application of the substance combination according to the invention or combined application of the substances, immunopharmacological enhancement of specific immunological reactions and defense mechanisms occurs. Meanwhile, induction of interleukin 2 receptor density/serum level concentration is also feasible and detectable in other cases of treatment. Obviously, TNF serum level increase, induction of TNF production is not only induced by the active substances of the mistletoe total extract, but this phenomenon hitherto not observed is associated with the clearing of remnants and antigens of dying tumor cells by macrophages. At the time of immunotherapy, there was about 200 to 300 g of tumor mass present in the organism of the above patient. Thus, induction of TNF production is not a characteristic feature of the immunotherapy principle described herein. With some patients, TNF serum level increase was observed, with others not.

From the work of Rosenberg et al., Washington, it follows that here, peripheral or preferredly tumor-infiltrating lymphocytes under the influence of interleukin 2 are grown in cell cultures in vitro, and are extensively transformed to so-called lymphokine-activated killer cells (LAK) which, in portions of 100 g, are re-infused into the patient, supplemented by further application of low-dosed interleukin 2. There are some indications that mitogenic immunostimulation according to the present invention triggers a similar process in vivo, though with less effort, but with the same clinical effectiveness.

There are some positive aspects in applying additional interleukin 2 for further support of therapy, in low doses, since the effect according to the invention is triggered faster by it, and hence, works like a starter.

Thus, first of all, object of the present invention are combination preparations for tumor therapy with controlled and regulated immune system, containing
 a) mitogenically immunostimulating substances; and
 b) thymomimetic substances.

In many cases, however, invariant combination preparations will not be used, but there will be conducted a tumor therapy with controlled and regulated immune system by applying effective amounts of
 a) at least one mitogenically immunostimulating substance; and
 b) at least one thymomimetic substance.

Thus, another object of the present invention is the use of mitogenically immunostimulating substances for the preparation of drugs for the combined application of same with thymomimetic substances in tumor therapy with controlled and regulated immune system.

Preferably, lectins or lectin-containing extracts are used as mitogenically immunostimulating substances. These extracts may originate from plants or animals. Preferably, also lectins regarded as being toxic hitherto may be employed. A form of application being present already and useful in practice is the lectin-containing mistletoe total extract.

As for thymomimetic substances, thymus extracts, synthetic thymus peptides, or thymomimetically active peptide fragments can be considered.

Both components are always dosed in such way that significant activity results. This is controlled by examining the usual serum parameters.

A further object of the present invention is a procedure for improved control of the immune system prior to and during tumor therapy, characterized in that several antigen doses of differing amounts are used in conducting the leukocyte migration inhibition assay (LMI) and /or the leukocyte adherence inhibition assay (LAI) to measure T-cell-dependent, adoptive, tumor-associated immunity ex vivo/in vitro.

If, for instance, the mitogenic lectin of a snake toxin is used which is β-galactose-specific and calcium-ion-dependent, it exhibits a very strong T-lymphocyte-specific mitogenic activity in vitro and in animal experiments, actually stronger than PHA, the standard stimulant lectin for T cells. If this lectin is used in animal experiments, for example with rabbits, and the intensity of the T-cell-dependent, antibody-mediated, cellular immune reaction is measured against varidase (streptokinase/streptodornase) in the LMI assay, against ubiquitous bacterial metabolites, then the typical reaction form of immune response enhancement in the LMI assay is obtained, i.e., strong increase of migration inhibition. Thus, this lectin, too, in animal experiments—like mistletoe total extract in humans—exhibits defense-cell-consuming properties in the process of immune response/immune defense enhancement, so that, also in subsequent clinical application of this mitogenic inductor, a suitable thymomimetic substance must be co-employed in combination, in order to be able to compensate iatrogenic lymphopenia, and to bring about clinical-therapeutic immune response enhancement. Here again, it must be pointed out that neither by using low-dosed mistletoe total extract nor the isolated active substances xyloglucan and ara-binogalactan, an immunotherapeutic concept can be realized. Both substances are acting selectively only upon granulocytes and macrophages, and do not measurably influence the tumor-associated immune reaction in the LMI assay ex vivo/in vitro and therefore do not exhibit any clinical effect upon cancer action, once the disease is manifest. Thus, it is not necessary to dose the mistletoe total extract in an amount where it is really acting mitogenically immunostimulating.

While intravenous application of mistletoe total extract/PLENOSOL, or a similar active substance/mixture of active substances is the preferred form of application, the same effects (though systematically weaker, and more locofocally, stronger effective in the lymph outflow area of the application location) are determined, if the active substances are applied subcutaneously or intramuscularly. For a thymomimetic substance such as TIMUNOX, the preferred way of application is subcutaneous. Likewise known and common is intravenous administration.

In galenic terms, mistletoe total extract/PLENOSOL, may be placed into the same ampoule together with the active substance of the preparation TIMUNOX, the pentapeptide TP5. Nevertheless, this drug combination mostly will be put on the market and promoted separately and/or in a combination pack for the new indication. Placing the active substance/mixture of active substances according to the invention into one ampoule with invariantly predetermined doses/active substance ratios would complicate an individually adjusted immune response enhancement in practice.

Known mistletoe preparations in the German language area are: ISCADOR, PLENOSOL, ABNOBA-VISCUM, HELIXOR, ISOREL. Known thymus preparations, thymomimetically active preparations in the German language area are, for instance: THYM-UVOCAL, total thymus preparation of Deutscher Thymusverein e.V., TP1, TIMUNOX, just to name the most important and effective ones being offered which are parenterally applicable.

Thymus preparations such as coated tablets, capsules, suppositories offered for peroral therapy are mostly thymus total extracts, and mostly are only very weakly thymomimetically effective in vivo. Thus, for the realization of the substance combinations described and for the realization of the therapeutic principle, they cannot be preferredly recommended and utilized.

BRIEF DESCRIPTION OF THE DRAWINGS

FIGS. 1 to 7, table 1, as well as the corresponding descriptions (annexes 1 to 3) illustrate the course of disease and therapy with the above patients in detail.

Figure 1:
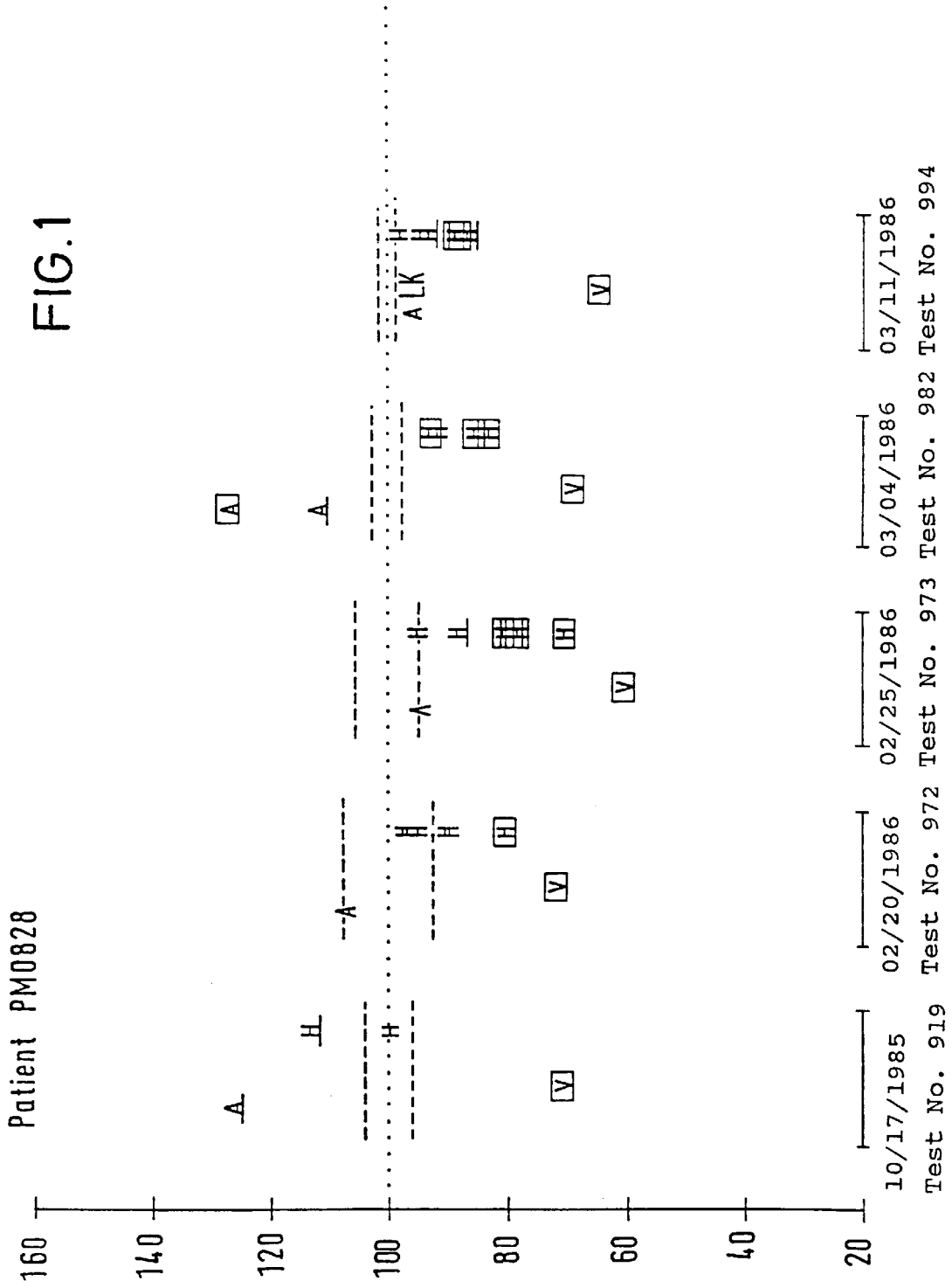
Figure 2:
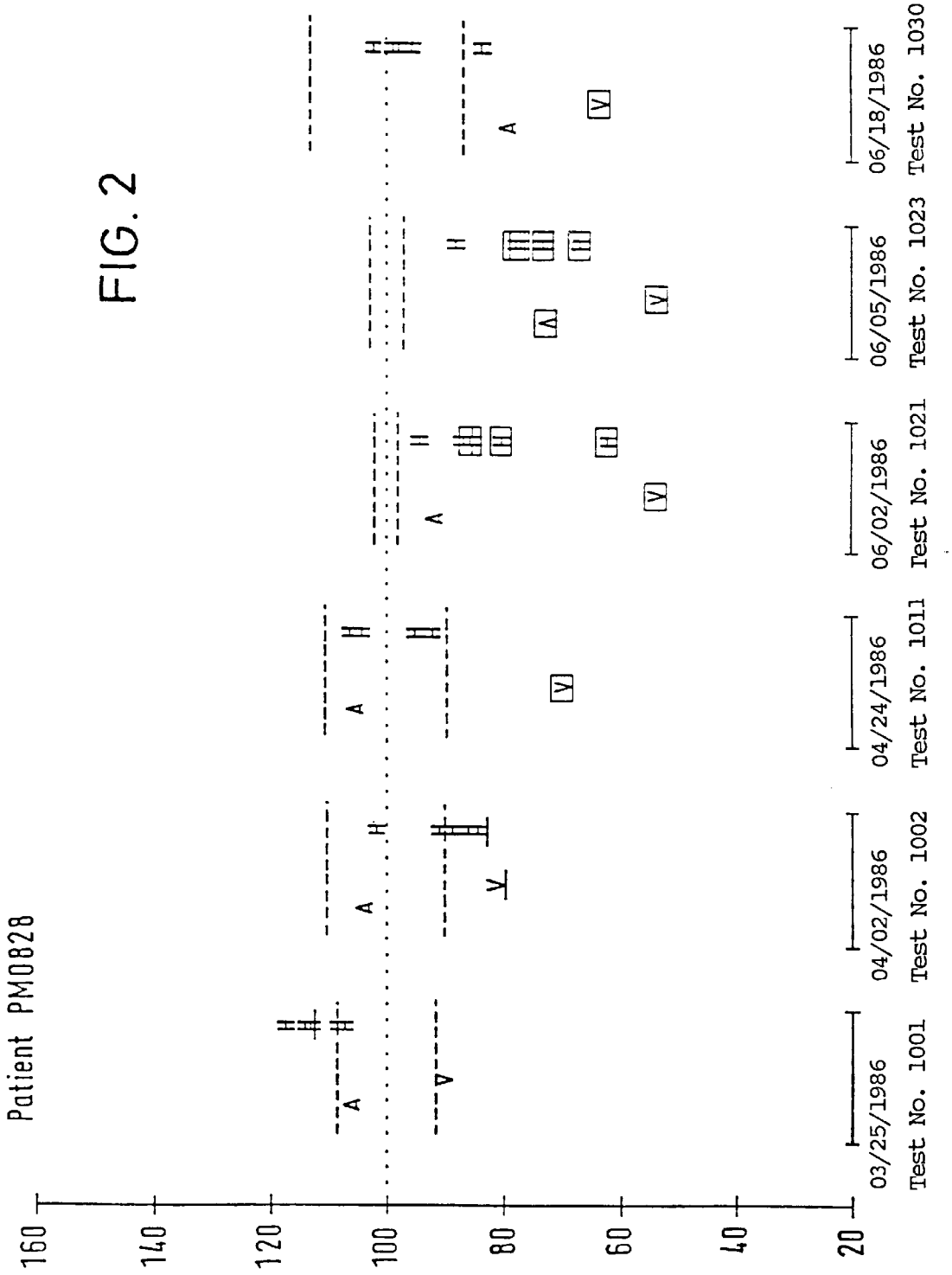

Meanwhile, an intense literature study of the work of H. Franz was done: Inhaltsstoffe der Mistel (Viscum album L.) als potentielle Arzneimittel, Die Pharmazie 40, 97–104 (1985). It contains a comprehensive survey up to 1985, concerning the state of knowledge about active substances in mistletoe extract and mode of action of these components.

More recent related work, for example by T. A. Khwaja et al.: Recent Studies on the Anticancer Activities of Mistletoe (Viscum album) and Its Alkaloids, Oncology 43, Suppl. 1, pp. 42–50 (1986), does not bring substantial progress. While in this work and in cited works by the same authors, effectiveness of mistletoe extracts and ingredients of mistletoe extracts are excellently substantiated using animal experiments, including the fact that the active ingredients in commercial preparations of German language countries vary by a factor of 10 to 1,000, the authors do not recognize the active principle that in vivo, direct tumor cell inhibiting/tumor cell killing activity of the ingredients is not effective, since active substance concentrations necessary for this purpose are hardly obtained in vivo. Effectiveness is solely founded on immunological basis.

The 1986 work by T. Hajto et al.: Natural Killer and Antibody-Dependent Cell-Mediated Cytotoxinic Activities and Large Granular Lymphocyte Frequencies in Viscum album-Treated Breast Cancer Patients, Oncology 43, 93–97 (1986), comprises work of known state of knowledge relating to immunological action of mistletoe extracts, here specifically with Iscador. In Germany, Iscador is the best selling mistletoe preparation, however, according to examinations by T. H. Khwaja, having the lowest lectin content per mg fresh plant weight. Due to the preparation process (fermentation), the active lectin substances are most extensively destroyed, and damage is done to their biological activity.

Subsequent to the day of application of the present invention (priority dated Jun. 1, 1989), the work of T. Hajto, K. Hostanska, and H. J. Gabius, Modulatory Potency of the β-Galactoside-Specific Lectin from Mistletoe Extract (Iscador) on the Host Defense System in Vivo in Rabbits and Patients, Cancer Research 49, 4803–4808, was published on Sep. 1, 1989. This work confirms the recognitions of the present invention that the immunopharmacologically relevant active substances of mistletoe extracts/mistletoe preparations are said mistletoe lectins and, above all, mistletoe lectin I. Nonetheless, the authors do not recognize the interrelation that mistletoe extracts/mistletoe lectin therapy, when applied immunopharmacologically in adequate doses, is lymphocyte-consuming, and independently, for full development of clinically effective therapy, leads to mitogenic immunostimulation, where additional administration of a suitable thymomimetic substance is necessary.

Likewise, the activity of interleukin 2 has been confirmed by further results. Systematic examinations unambiguously showed that the immunopharmacological major activity of mitogenic immunostimulation consists in the additive effect of lectin inductors and thymomimetic substance(s), such that firstly, the thymomimetic substance (TP5 and/or TP4/TP3)

a) increases total lymphocyte number and total T cell number, b) improves helper/suppressor cell ratio in favor of the helper cells, c) activates the lymphocytes (=increase of the number of HLA-DR-positive and/or transferring receptor positive lymphocytes), and secondly, the lectin inductors with high significance increase a) the number of interleukin 2 receptor positive lymphocytes throughout several functional subgroups of lymphocytes including natural killer cells, b) but mainly the number of cytotoxic lymphocytes (=CTL), c) the total number of natural killer cells (=NK cells) not being substantially influenced.

The induced shift in composition of functional subgroups of the lymphocytes is also depending on the quality of tumor-associated immune response/defense reaction. While activation of the NK cell system can be detected, similarly as described by other authors (T. Hajto et al., 1986, and T. Hajto et al., 1989), the major domain/major mode of activity of mitogenic immunostimulation is an exponential enhancement of cytotoxic lymphocyte functions (T-cell-dependent cellular cytotoxicity CTL) and antibody-controlled cellular cytotoxicity (ADCC reaction), with break of immune tolerance in the tumor-associated immune response in clinically manifest cancer disease. Accordingly, in the course of treatment, there is produced a typical picture of each of the functional subgroups of lymphocytes depending on the quality of tumor-associated immune response (cf. table 2).

In clinically manifest cancer disease with metastases, a measurable, verifiable curing effect by mitogenic immunostimulation is detectable only then when in the autologous test system in the leukocyte migration inhibition assay (LMI) in its optimized form, a positive, T-cell-dependent, adoptive, tumor-associated immune reaction is present ex vivo/in vitro. The stronger and marked this ex vivo/in vitro measurable tumor-associated reaction, the higher the therapeutic potential of mitogenic immunostimulation. This statement is confirmed by the further course of disease and treatment with breast cancer patient ME 1015, described in annex 3, and in the further course in annex 4 and FIG. 7 (to annex 4).

This does not exclude that mistletoe extract therapy and hence, mitogenic immunostimulation results in a positive, clinical therapy effect also in such tumor treatment cases where no reaction can be measured in the LMI assay, and tumor-associated immune reaction is present only on the level of macrophages, NK cells. Such positive clinical-therapeutic effect, however, should be of pragmatical importance only in post-operative, adjuvant treatment cases where just few tumor cells and micrometastase foci are present. A curing effect can probably be proven only by adjuvant therapy studies, and not by considering individual treatment cases.

Annex 1

Breast cancer patient ZO, A1287 60 years old.

Operation theater Dec. 21, 1988 SS, ablatio mammae li. PT3, PNo, Mo, G3

Primary tumor diameter more than 5.0 cm. Lymphangiosis carcinomatosa in the tumor bed.

| | |
|---|---|
| Cytosol-CEA | 3.63 ng/mg tum.prot. |
| Cytosol-Ca-15-3 | 57.32 ME/mg tum.prot. |
| ytosol-TPA | 1046.60U/mg tum.prot. = highly positive, growing fast. |
| Estrogen receptors | 98 femtomol/mg tum.prot. |
| Progesterone receptors | 75 femtomol/mg tum.prot. |

3 cycles-GMF+24 months Tamoxifen therapy according to BMFT [Department for Research and Technology] breast cancer study between the chemotherapy cycles and subsequently 4 weeks Timunox® immune protection, immune restoration, begin of chemotherapy, however, not before 14th day postop.

Dec. 21, 1989 Operation theater day, enhancement, as to be expected, with the tissue section technique at good general immunity (V). Gp-55 cross reactivity (biotype A of breast carcinoma).

Jan. 5, 1988 at 14th postop. with high-grade inhibition with all cytosol and sediment antigen doses, good recall immune response.

| | |
|---|---|
| 02/02/1988 | 1. day II. chemotherapy cyle. |
| 03/02/1988 | 1. day III. chemotherapy cycle. |

Increasing disappearance, extinction of high-grade tumor-associated immune status/immune response even by 3 cycles of CMF with the 61-year-old postmenopausal patient. Cave course in general (recall) immune response in spite of Timunox therapy.

Apr. 8, 1988, 5 weeks after 1st day of last chemotherapy cycle. Up to this time, only immune restoration using Timunox 100, 2 to 3×1 ampoule subcutaneous. This day, total T cell number 80% (normally from 58–75%), with total lymphocyte number of 2100/cmm. Helper cells 59%, suppressor cells 23%, NK cells 15%, i.e., in spite of normal subpopulations high-grade infliction of tumor-associated immune reaction by chemotherapy, by 3rd cycle CMF, this in spite of Timunox therapy.

Apr. 20, 1988 to Jun. 29, 1988, 1st mitogenic immunostimulation treatment. High-grade enhancement of tumor-associated immune reaction versus dissolvable cytosol antigen fraction (possibly versus viral gene products), however, no longer measurable tumor-associated immune reaction versus sediment/cell membrane antigen fraction, although same antigen preparation was employed postoperatively on Jan. 5, 1988.

Note: This is a typical reaction to chemotherapy with biotype B breast cancer in postmenopause: most of the antigenicity originates from the cell interior. Tumor-associated immune reaction versus cell wall antigens is stronger, more markedly inflicted by chemotherapy.

Aug. 10, 1988 to Sept. 19, 1988, 2nd mitogenic immunostimulation therapy cycle. In spite of immune enhancement, only slight, measurable tumor-associated immune reaction (only single significant) versus smallest antigen dose (cytosol 4 µg/ml), with most powerful enhancement of general immune reaction versus recall antigens employed. (V sign)

Note: According to present state of knowledge, further mitogenic immunostimulation is not indicated. Active-specific immunostimulation/vaccination with this patient were indicated at this point, with such high a residual risk.

Annex 2

Patient ML0621 63-year-old breast cancer patient

DEMONSTRATION OF COMPARATIVE EFFECT/MONITORING OF THYMUS MONOTHERAPY (TIMUNOX) VERSUS MITOGENIC IMMUNOSTIMULATION INTRAINDIVIDUALLY

Please gather patient data from the insert.

Supplement

Primary therapy in September 1985. At that time, pT2, primary tumor diameter 3.9 cm, 11 affected axillary lymphatic nodes. Estrogen and progesterone receptor concentration at limit value.

Sep. 26, 1985, first LMI on 14th day postop., i.e., subsequent to application of 1st perioperative adjuvant chemotherapy cycle on 1st and 8th postop. day according to BMFT breast cancer study therapy record 2. According to this, no longer measurable tumor-associated immune reaction, with good general immunity (V sign).

Note: Cave poster lecture of the working group at annual congress of Deutsche Krebsgesellschaft in March 1986 at Munich. It could be verified there, with about 40 cases, that by chemotherapy, even subsequent to a perioperative chemotherapy cycle, tumor-associated, T-cell-dependent, measurable immunity is inflicted, negatively influenced significantly, in high grade.

After IVth chemotherapy cycle, termination or adjuvant chemotherapy due to intolerance, lympho-leukopenia, with high probability on the ground/reactivation of a virus infection.

Apr. 1, 1987, brief stat. examination. Here, measurable tumor-associated immunity versus primary tumor tissue (frozen section technique) with continuing very bad general immunity (V).

Dec. 21, 1987: Increasing tumor marker values Ca-15-3 and TPA. CA-15-3 pathological, above 32 mE/ml. CEA normal (tumor was cytosol CEA negative, possibly biotype B, gp 55 immune response could not be tested).

Build-up of high-grade, tumor-associated immune reaction, in the course of beginning progression, however typically, as to be expected theoretically and practically, with enhancement, alkaline phosphatase, gamma-GT, liver sonogram, roentgenologically/clinically NAD (AP, G-GT, roentgen thorax, bone scintigram, ultrasound liver).

According to recent recognitions, indication for secondary therapeutic measures

From February 1988 till Apr. 7, 1988, only Timunox monotherapy: 2–3 ampoules of Timunox 100 subcutaneous, depending on hemogram status and status of functional subgroups of lymphocytes (total T cells, helper, suppressor cells and NK cells).

Apr. 7, 1988: Significant improvement of general ability of immune response to recall antigens (V). Significantly measurable effect of thymus/Timunox monotherapy on tumor-associated immune reaction in LMI assay, however, without overcoming enhancement/immune tolerance.

April 20 till Jun. 29, 1988: 1st mitogenic immunostimulation. In this fashion, combination of test preparation (150348), a mistletoe extract including standardized mistletoe lectins I+II+III and with standardized mitogenic activity/biological activity, high-grade increase of general immune response and break of enhancement, immune tolerance both versus primary tumor and lymphatic node metastase tissue as antigen source (frozen section technique) for the LMI.

Tumor marker courses (Ca-15-3, MCA, TPA) of Dec. 21, 1987 to February 1988, to Apr. 7–Apr. 20, 1988 and to Jun. 29, 1988 verify that during mitogenic immunostimulation, by this sole therapy, within 6–8 weeks, significant degradation of tumor material results, here, to 30%.

Note: With metastasizing breast cancer and progression begun, hormone immunotherapy and above all, chemo-immunotherapy is preferred, however, because this is much more effective than chemotherapy alone, or immunotherapy (mitogenic immunostimulation) alone. For the time being, no general recommendations can be given here; therapeutic decisions must be made individually!

Annex 3

Patient ME1015 75-year-old breast cancer patient

Breast carcinoma, primary therapy in February 1985. At that time, PT3, N4, Mo, primary tumor diameter more than 5.0 cm, 22 affected lymphatic nodes. Estrogen and progesterone receptors positive. Cytosol CEA concentration 8.7 ng/mg tumor protein.

Serum CEA 47.9 ng/ml preop., 28.0 ng/ml postop., after 2½ cycles CMF, 22.0 ng/ml, after beginning effectiveness of adj. Tamoxifen therapy in autumn 1985, 28.0 ng CEA/ml.

Primary therapy: Ablatio mammae, 2½ cycles CMF, then, from June 1995 on, constant Tamoxifen therapy to beginning ineffectiveness. Within the period November 1985 till March 1988, i.e., more than 2½ years, stable serum CEA values of between 27 to 32.0 ng CEA/ml. Intermediate stepped CEA increase only during/after repeated severe, feverish cystopyelitides, however, no possibility to objectify immune parameters during these diseases.

From March 1988 to July 1988, beginning exponential serum CEA increase/progression to 48 ng CEA/ml. For this reason, appointment to therapy rearrangement/extension:

On Aug. 1, 1988, serum CEA already 68 ng/ml (EIA Hoffmann LaRoche). For therapy and further progress, see below.

Demonstration of change in tumor-associated immunity

Feb. 26, 1985 LMI assay on 14th day postop.
May 20, 1985 LMI assay after 2½ cycles CMF. Interpretation After removal of major tumor mass and possibly after elimination of circulating immune complexes which may form the basis for suppressor activities such as enhancement, positive tumor-associated immune reaction versus primary tumor and lymphatic node metastase tissue, and inhibition, with good general immunity (V).

Note: Here, there possibly might be indication for ASI (ASI=active specific immunostimulation, i.e., suitable vaccination).

Due to additional positive increase of present tumor-associated immunity, without negative prognosis such as enhancement, further course of the disease might be influenced favorably, particularly, in combination with Tamoxifen.

Aug. 1, 1988: High-grade enhancement in the course of begun tumor progression. Deterioration of general immunity. Lip cyanosis, possibly due to beginning lung carcinosis and effect of circulating immune complexes. In the further course (patient, from Aug. 1, 1988 on, received a total of 3 cycles of mitogenic immunostimulation in standard dosage: 1×1 ampoule Plenosol®, intensity II per week, intravenous, and 2 to 1 ampoules Timunox 100, subcutaneous) CEA serum level decreased during any of the 6 week immunotherapy cycles by 30 to 40%, from 41 ng/ml to 28 ng/ml, and then, down to 16 ng/ml until April 1989. Serum CEA level normal up to 5 ng/ml. During therapy pauses, between the immunotherapy cycles, hormone therapy (Tamoxifen or highly dosed Medroxyprogesterone acetate) and chemotherapy (Mitomycin C), respectively, were employed clinically without success, without therapeutic effect. In this treatment case, therapeutic potency of mitogenic immunostimulation can be verified drastically: immunotherapy is highly effective, though all the other tradition-medicinal therapeutic possibilities have already become ineffective (lips notably turning rosy). Clinically-roentgenologically, no evidence of disease at this time yet. Nonetheless, rearrangement/supplementation of therapy, since the conducted multi-parameter study shows that such constellation of findings is equivalent to or represents a death sentence, and passivity/waiting is ethically irresponsible today.

Sep. 19, 1988. Due to mitogenic immunostimulation (in the course of therapy rearrangement), overcome of enhancement/immune tolerance and powerful increase of general immunity (V sign). CEA on Sep. 19, 1988 about 41 ng/ml.

Annex 4

Patient ME1015 75-year-old breast cancer patient (further course of disease and treatment in the case described in annex 3 and FIG. 6)

Originally, prior to begin of immunotherapy/mitogenic immuno-stimulation on Aug. 1, 1988, the CEA serum level (=tumor marker) was 68.0 ng/ml. This is a highly pathological value: normally, it is 5.0 ng CEA/ml.

In the period from Aug. 1, 1988 till November 1989, patient passed a total of 5×6 weeks mitogenic immunostimulation with 1×20 clinical units of mitogenic inductor from mistletoe extract, intravenous bolus weekly, and 2×50 mg TP5 (=Timunox®), subcutaneous. Till November 1989, serum CEA level dropped to 6.5 ng/ml. During another 6 week treatment, serum CEA level could not be decreased any further. A pause in therapy followed. During this pause in therapy, steady and continuous re-increase of tumor marker serum level CEA and Ca-15-3 occurred after a short while (Ca-15-3 progress not represented here).

On Mar. 21, 1990, the serum CEA level reached the value of 14.8 ng/ml again.

On Mar. 27, 1990, tumor-associated immunity in the LMI assay was tested again (see FIG. 7). V=representation of immune reaction versus recall antigens streptokinase/streptokinase for registration of general immunity conditions. A=representation of tumor-associated immune reaction versus autologous tumor tissue: PT=primary tumor, LK=lymphatic node metastase. Here, the old 20μ frozen section technique of the LMI assay as antigen source has been applied.

From Mar. 27, 1990 on, patient again received a mitogenic immunostimulation treatment as described above. According to the very weak tumor-associated reaction versus LK tumor tissue being significant only once, the effect of immunotherapy was a mere cease of progression, as can be seen from CEA serum levels determined weekly.

| Serum CEA level | on 03/27/90 | 14.80 ng/ml |
| --- | --- | --- |
| | on 04/16/90 | 14.07 ng/ml |
| | on 04/23/90 | 14.46 ng/ml |
| | on 04/30/90 | 17.06 ng/ml |
| | on 05/07/90 | 14.32 ng/ml |
| | on 05/12/90 | 14.75 ng/ml |

From this, like from several similar treatment cases, the recognition may be derived that firstly, effectiveness of mitogenic immunostimulation is dependent on quality and intensity of the tumor-associated immunity measurable ex vivo/in vitro, and secondly, in future, this form of cancer immunotherapy preferably must be combined with another form of tumor immunotherapy, with an autovaccination method such as active specific immunotherapy (=ASI), so that long-term complete remission or complete cure can be achieved.

Annex 5
Patient ME1015 75-year-old breast cancer patient
(further course of disease and treatment in the case described
in annexes 3+4 and FIGS. 6+7)
Here: Demonstration of additional therapeutic effect and mode of effectiveness of mitogenic immunostimulation if the double drug combination (mitogenic inductor from Viscum album extract+synthetic thymus peptide/TP5= Timunox®) is expanded to a triple drug combination using low-dose interleukin 2.

From May 14, 1990 (Monday) on, patient received the following therapy:

- 1×20 clinical units of mitogenic inductor 150348 from Viscum album extract weekly, intravenous bolus (x);
- 3×50 mg TP5 (=Timunox®) weekly, subcutaneous, on Monday, Wednesday, Friday;
- 3×3.0 millions of interleukin 2/qm body surface weekly, i.e., here, each 5.0 millions I.U. Proleukin, (manufactured and traded by Eurocetus GmbH, D-6000 Frankfurt/Main) as long-term infusion for 4 hours, each week on Monday, Wednesday and Friday;

for a total of 2 weeks.

| Serum CEA level course | on 05/12/90 | 14.40 ng/ml (in repetition) |
|---|---|---|
|  | on 05/14/90 | 14.75 ng/ml |
|  | on 05/21/90 | 10.10 ng/ml |
|  | on 05/28/90 | 7.05 ng/ml |

Composition and changes of functional subgroups of lymphocytes:

|  | On 05/14 | On 05/21 | On 05/28 | Normal | Values |
|---|---|---|---|---|---|
| Total lymphocytes | 1150/cmm | 1350/cmm | 1470/cmm | above | 1200/cmm |
| Total T cells | 68% | 73% | 77% | 58 | −73% |
| B cells | 25% | 21% | 15% | 11 | −17% |
| Helper cells | 32% | 36% | 42% | 20 | −45% |
| Suppressor cells | 25% | 20% | 18% | 12 | −25% |
| H/S cell ratio | 1.28% | 2.0% | 2.33% | 1.40 | −2.00 and above |
| NK cells | 9% | 10% | 14% | 7 | −15% |
| Activated T cells | 14% | 21% | 24% | 2 | −12% |
| CTL = cytotoxic T cells | 12% | 26% | 31% | 2 | −10% |
| Interleukin 2 receptor-positive natural killer cells | 1% | 2% | 5% | 1 | −4% |
| Interleukin 2 receptor-positive total T cells | 17% | 27% | 38% | 2 | −10% |

Note

The mitogenic inductor 150438 is an immunopharmacologically standardized mistletoe extract, based on lectin content as well as on the ability to significantly enhance T-cell-dependent, adoptive, cellular and antibody-dependent immune reaction versus recall antigens such as tuberculin, streptokinase/streptodornase in the leukocyte migration inhibition assay (LMI) in animal experiment in vivo.

The mitogenic inductor 150438 is a commercial preparation from Serobac, Institute for Oncology, D-5650 Solingen 11, P.O. Box 111,053. In the preparation, the ratio of mistletoe lectins to other active substances and bulk material is improved by a factor of 10–25 compared to usual commercial preparations in German language countries. Moreover, the preparation can be systematically applied intravenously, virtually without any side effects.

The mode of effectiveness of additionally low-dose applied interleukin 2 in the drug combination for mitogenic immuno-stimulation conducted and represented in this case example is a therapy-typical effect. Additional administration of low-dose interleukin 2 additively enhances the already highly active double drug combination.

TABLE 1

| Treatment Case P.M. 58 years old | 10/17/85 | 02/20/86 | 02/25/86 | 03/04/86 | 03/11/86 | 03/25/86 | 04/02/86 | 04/24/86 | 06/05/86 |
|---|---|---|---|---|---|---|---|---|---|
| Total lymphocyte number/mm$^3$ | 1880 | 1658 | 1380 | 1260 | 1080 | 930 | 1240 | 1480 | 1740 |
| Total T cell number, % | 52 | 61 | 58 | 51 | 44 | 38 | 47 | 57 | 68 |
| Number of helper cells, % | 38 | 31 | 28 | 20 | 18 | 16 | 26 | 30 | 32 |
| Number of suppressor cells, % | 21 | 20 | 16 | 15 | 15 | 12 | 15 | 18 | 18 |
| Helper/suppressor cell ratio | 1.80 | 1.55 | 1.75 | 1.33 | 1.20 | 1.33 | 1.73 | 1.66 | 1.77 |
| Number of natural killer cells, % | 11 | 8 | 9 | 10 | 10 | 7 | 10 | 12 | 15 |

Total T, helper, suppressor, NK cells determined using reagents of the company Becton-Dickinson, Heidelberg.
Method: direct immunofluorescence subsequent to preparation/isolation of lymphocytes.
Normal values: Total T cells 58–73%, helper/suppressor cell ratio above 1.40–1.80, NK cells 8–15%.

TABLE 2

| | Normal values with healthy subjects | Values (N = 12) with untreated breast cancer patients with metastases before therapy | (See note: x) Values (N = 6 + 6) after 6 weeks mitogenic immunostimulation | |
|---|---|---|---|---|
| | | | patients with CTL reaction | patients with ADCC reaction |
| Total lymphocytes | above 1200/cmm | 780–1880/1150 (xx) | | |
| Total T cells | 58–73% | 38–66/59% | 68–83/73% | 42–68/62% |
| B cells | 11–17% | 7–21/14% | 4–17/10% | 18–37/25% |
| Helper cells | 20–45% | 17–28/23% | 22–51/34% | 19–40/33% |
| Suppressor cells | 12–25% | 18–35/25% | 8–22/17% | 10–36/23% |
| Activated T cells | 2–12% | 0–3/1% | 17–27/21% | 14–20/15% |
| CTL = cytotoxic T cells | 2–10% | 0 0/0% | 21–53/36% | 13–27/14% |
| Natural killer cells (=NK) | 7–15% | 6–17/9% | 9–18/15% | 8–17/14% |
| Interleukin 2 receptor positive NK cells | 1–4% | 0–0/0% | 1–4/3% | 1–3/2% |
| Total interleukin 2 positive T cells | 2–10% | 0–2/0% | 18–38/27% | 6–22/17% |
| Helper/suppressor cell ratio | above 1.40–2.00 | 0.55–1.8/0.9 | 1.30–2.7/1.95 | 0.70–1.95/1.4 |

Note:
(x) Therapy, i.e., mitogenic immunostimulation, with this group of breast cancer patients, was effected for 6 weeks with 1 × 40 clinical units of mitogenic inductor 150438 from Viscum album extract, intravenous bolus weekly, and 3 × 50 mg TP5 (=Timunox$^R$), subcutaneous, weekly. Examinations were conducted before therapy was started and exactly one week after last mistetoe extract application.
(xx) Here, the range of measured results and each median value is given.
Examinations were carried out using the FACS apparatus of the Company Becton-Dickinson and monoclonal antibodies of the same company according to the above working guideline with up to triple immunofluorescence stainings of individual examination batches to ensure the above, more extensive splitting of functional subgroups of lymphocytes.

Explanations for FIG. 3

Patient No. 0828 P.M., female, 58 years old, diagnosis: metastasizing breast cancer Demonstration of relationship between reaction intensity of T-cell-dependent, antibody-controlled, complement-dependent, tumor-associated immunity, measured in leukocyte migration inhibition assay, and in vivo mitogenically induced lymphokine serum level, here: tumor necrosis factor and interleukin 2 receptor serum level in serum of breast cancer patient, measured using the BIOKINB* TNF test kit and the CELLFREE* interleukin 2 test kit of the company T-Cell Sciences, Inc., 840 Memorial Drive, Cambridge, Mass, U.S.A. To measure T-cell-dependent adoptive tumor-associated immunity in leukocyte migration inhibition assay (LMI assay), processed cytosol remnants (dissolvable tumor antigen fraction) and tumor sediment remnants (non-dissolvable cell membrane/cell wall antigen fractions) were utilized as the autologous tumor antigen source.

Mitogenic immunostimulation is an innovation by Serobac®, Institute for Oncology, 5650 Solingen 11, P.O. Box 111,053, Germany.

The high-grade in vivo induction of TNF and interleukin 2 was at the toxicity limit using the test substance 150348 by This is a plant lectin mixture being less toxic in vivo or Con-A from the group of known in vivo lymphokine conductors.

Highest TNF serum level with blood donor:
  67 g/ml (N=136)
Highest IL-2R serum level with blood donor:
  477 U/ml (n=174)

I claim:

1. A method of inhibiting metastatic breast cancer, which comprises administering
  a) at least one mitogenically immuno-stimulating substance and
  b) at least one thymomimetic substance,
wherein the mitogenically immuno-stimulating substance is mistletoe extract and the thymomimetic substance is thymus extract in amounts effective to inhibit metastatic breast cancer.

* * * * *